US00PP24579P3

(12) United States Plant Patent
Dodd et al.

(10) Patent No.: US PP24,579 P3
(45) Date of Patent: Jul. 1, 2014

(54) APPLE TREE NAMED 'MAIA1'

(50) Latin Name: *Malus×domestica*
Varietal Denomination: MAIA1

(75) Inventors: William Dodd, Newcomerstown, OH (US); David Doud, Wabash, IN (US); John Mitchell Lynd, Pataskala, OH (US); Gregory Miller, Carrollton, OH (US)

(73) Assignee: Midwest Apple Improvement Association, Newcomerstown, OH (US)

( * ) Notice: Subject to any disclaimer, the term of this patent is extended or adjusted under 35 U.S.C. 154(b) by 91 days.

(21) Appl. No.: 13/573,033

(22) Filed: Aug. 15, 2012

(65) Prior Publication Data

US 2014/0053301 P1 Feb. 20, 2014

(51) Int. Cl.
*A01H 5/00* (2006.01)

(52) U.S. Cl.
USPC ..... Plt./161

(58) Field of Classification Search
USPC ..... Plt./161
See application file for complete search history.

*Primary Examiner* — Susan McCormick Ewoldt
(74) *Attorney, Agent, or Firm* — Flynn, Thiel, Boutell & Tanis, P.C.

(57) ABSTRACT

A new and distinct variety of apple tree 'MAIA1' is described, derived from a cross of 'Honeycrisp' and 'Fuji'. This new variety is unique from parent 'Honeycrisp' by being harvested in mid-October, 6-8 weeks after 'Honeycrisp'. This new variety is unique from parent 'Fuji' by tree form, with 'MAIA1' being moderate vigor, more open tree canopy and higher spur density as contrasted with the bushy, tight tree canopy and lower spur density of 'Fuji'. 'MAIA1' blooms approximately one week later than parent 'Fuji'. 'MAIA1' fruit is moderate size, very crisp, sweet and long keeping, both in refrigerated storage and at room temperature.

3 Drawing Sheets

Latin name of the genus and species of the plant claimed: *Malus×domestica.*

Variety denomination: 'MAIA1'.

BACKGROUND OF THE INVENTION

A new and distinct variety of apple was identified from a population of seedlings derived from a cross of 'Honeycrisp' (U.S. Plant Pat. No. 7,197) and 'Fuji' (not patented—original strain originating from a cross of 'Delicious' and 'Ralls Janet' made in Japan and released as a variety in 1962). This cross was made as a part of an apple breeding project. This superior seedling tree was identified in a population of seedlings from this cross at Wabash, Ind.

The seedling tree was planted as a 1 year old tree at Wabash, Ind. in 2001 and grown among a population of several hundred siblings. Evaluations of fruit quality and tree growth parameters were begun in 2005 and this seedling was identified over several years as superior based upon tree growth habit, precocity, superior fruit quality and storability. Utilizing grafting reproduction on malling 7 rootstock (unpatented), the new apple tree variety was asexually propagated by David Doud in 2008 at Wabash, Ind. and has been observed to remain true to the description set forth herein.

The new variety, named 'MAIA1' is distinct from 'Honeycrisp' as 'MAIA1' ripens mid-October, 6-8 weeks after 'Honeycrisp' (Table 1). 'MAIA1' is distinct from 'Fuji' by tree growth habit, with 'MAIA1' being less vigorous, more open canopy, with increased number of fruit spurs per foot of 2 year wood (Table 2; FIG. 2). In addition, 'MAIA1' blooms approximately one week later than parent 'Fuji'. 'MAIA1' fruit (FIG. 3) are medium sized, extremely crisp, sweet (Table 3), with long storability.

BRIEF DESCRIPTION OF THE DRAWINGS

The accompanying photographs show typical specimens of the new variety as depicted in color as nearly true as is reasonably possible. 'MAIA1' photographs were taken at Wabash, Ind.; 'Fuji' photographs were taken at Pataskala, Ohio.

DETAILED BOTANICAL DESCRIPTION

Figure 1:
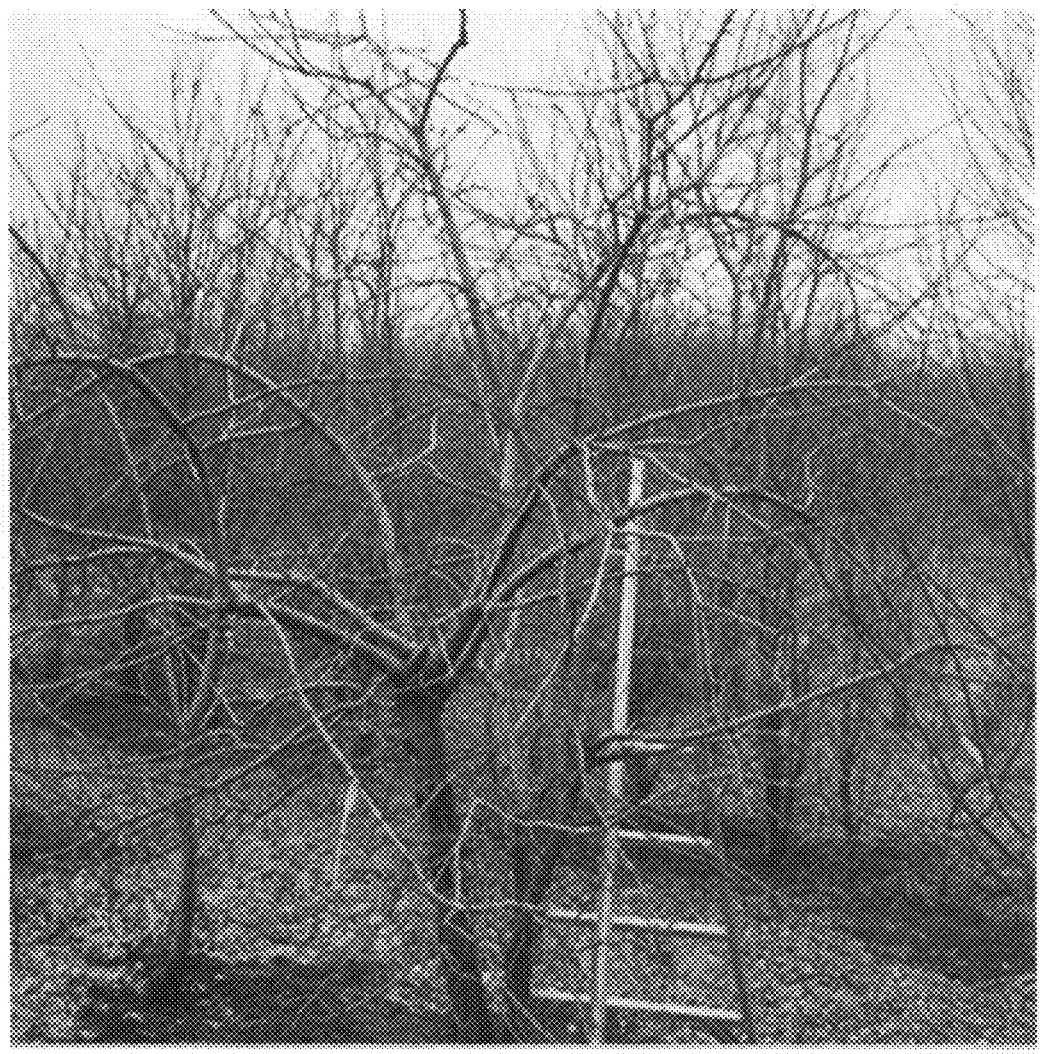
FIG. 1. Original seedling tree of 'MAIA1' showing open canopy and moderate tree vigor.
Figure 2:
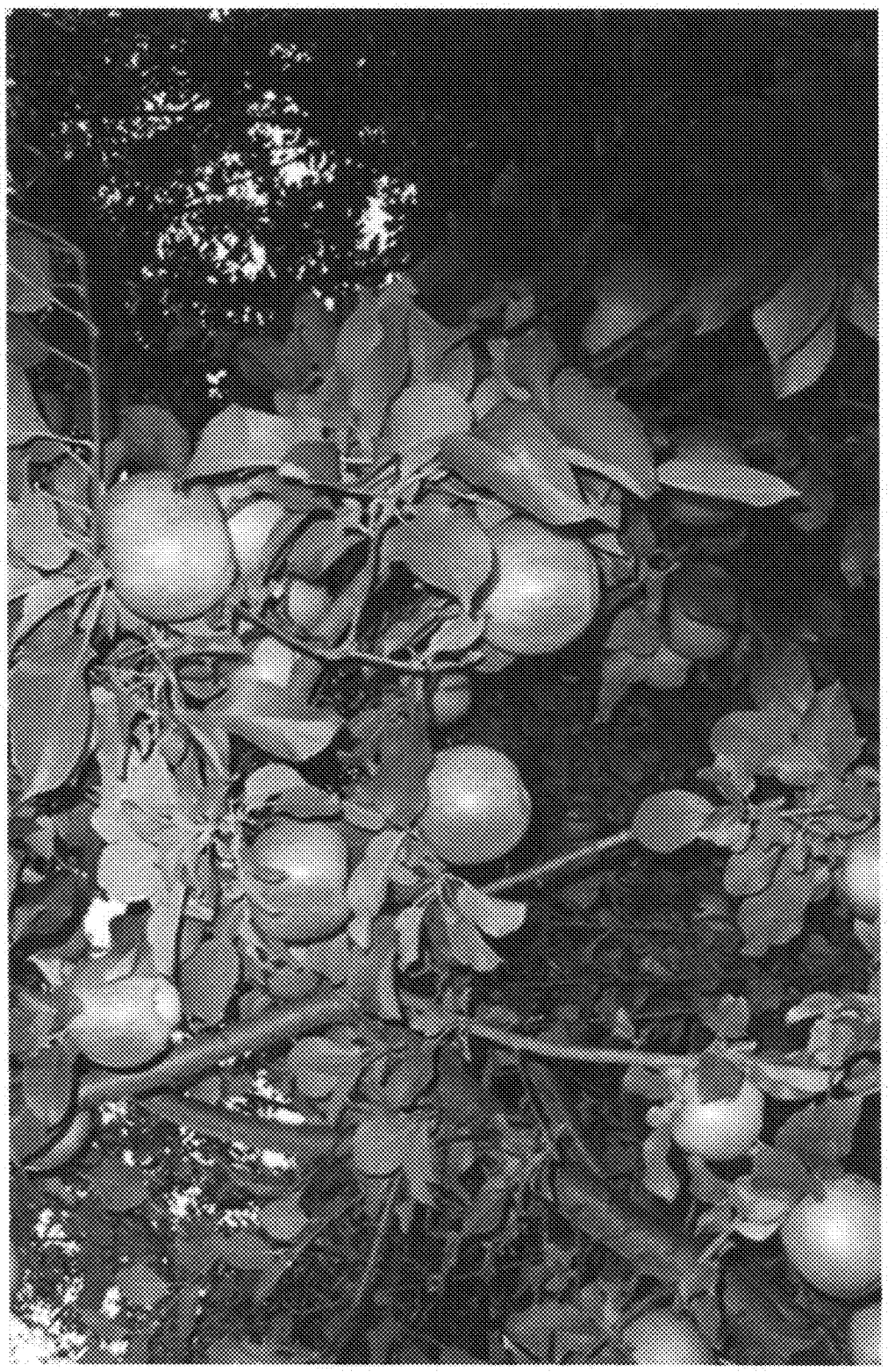
FIG. 2. One and two year old wood of original seedling tree of 'MAIA1', showing high spur density.
Figure 3:
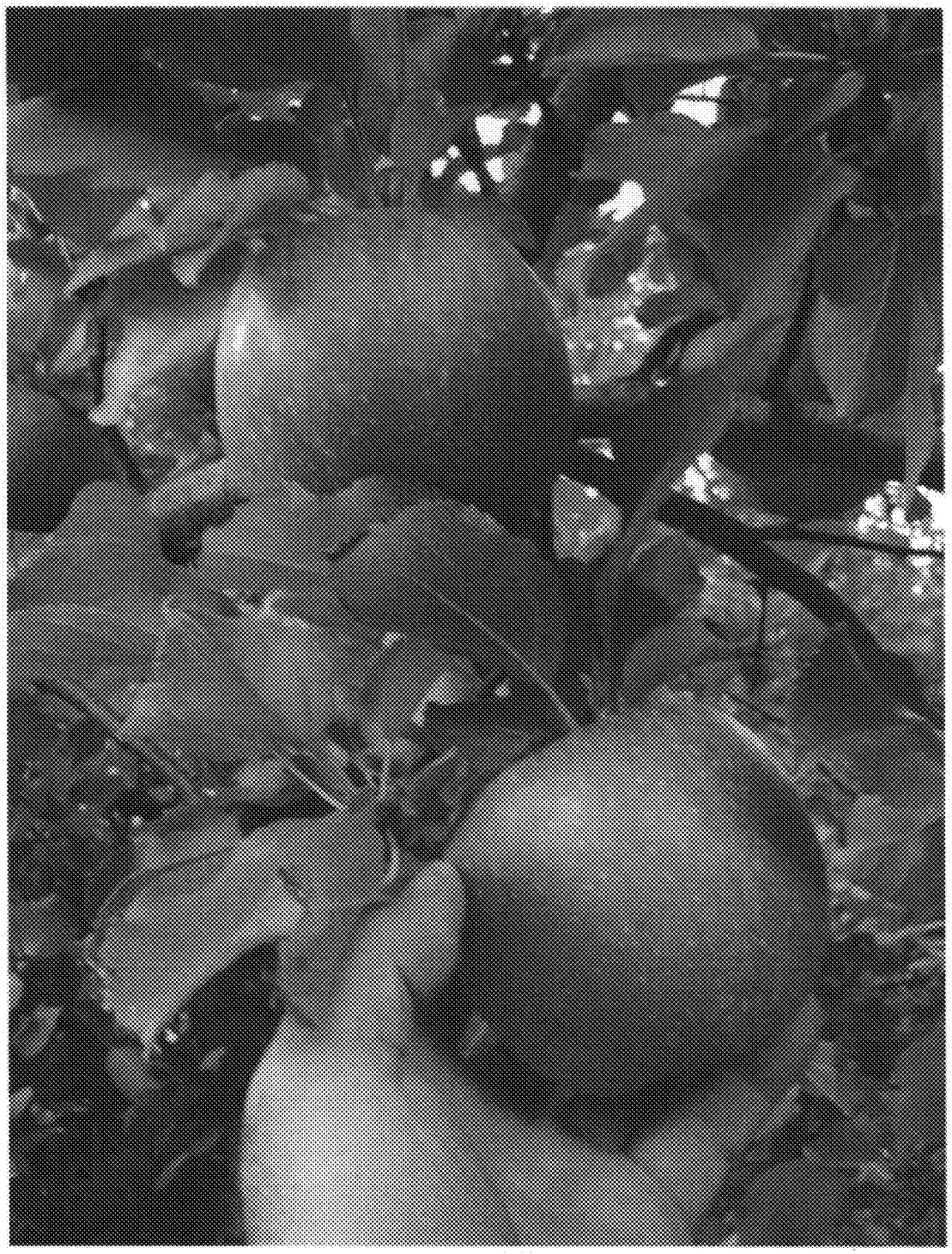
FIG. 3. Fruit of 'MAIA1' on the tree, October 2011.

Color references are made to The Royal Horticultural Society Colour Chart (R.H.S.) 2001 Edition.

Parentage: 'Honeycrisp' female parent and 'Fuji' male parent; controlled cross made at Pataskala, Ohio in 1999.

Original seedling tree:

*Age.*—12 years.
*Size.*—10' height, 10' spread.
*Vigor.*—Low to medium.
*Density.*—Medium.
*Form.*—Round, spreading.
*Production.*—Very productive; 2.5 bushels/tree @ 300 trees/acre=750 bushels/acre.
*Growth type.*—Non-spur; very weak dominance.
*Bearing.*—Annual.

Trunk:

*Original seedling tree size.*—13 cm in diameter at 15 cm height above the soil line.
*Bark color.*—Grey-Brown 199A.
*Lenticels.*—Oblong, 1.5 mm×2.5 mm.

*Lenticel color*.—Grey-Brown 199B.
*Lenticel density*.—6 lenticels/cm$^2$.

Branches:
3 *year old*.—16-22 mm in diameter, branch angle 80-90°, Grey-Brown 199A.
2 *year old*.—14-18 mm in diameter, branch angle 80°-90°, Grey-Brown 199A.
1 *year old*.—9-10 mm in diameter, branch angle 80°-90°, Grey-Brown 199D.

Leaves:
*Size*.—Length 75 mm; width 55 mm.
*Texture*.—Leathery, crisp.
*Form*.—Ovate.
*Base*.—Roundly cuneate.
*Apex*.—Acute.
*Adaxial surface pubescence*.—None.
*Abaxial pubescence*.—Finely pubescent.
*Adaxial surface color*.—Yellow-Green 146B.
*Abaxial surface color*.—Yellow-Green 146D.
*Venation*.—Pinnate, 8-9 major veins; mainly alternate; Yellow-Green 149D.
*Margin*.—Serrate.
*Petiole length*.—30 mm.
*Petiole width*.—3 mm.
*Petiole abaxial color*.—Yellow-Green 145A to Greyed-Purple 185C toward base and abscission layer on larger leaves.
*Petiole groove*.—Very shallow, depth 0.1 mm.
*Stipules*.—Present; 5 mm length; 1 mm width; Yellow-Green 146D.
*Leaf glands*.—None observed.

Leaf buds:
*Length*.—Length 1.5 mm.
*Width*.—1.5 mm.
*Color*.—Yellow-Green 145B with Greyed-Purple 185B overtones.
*Placement on branch*.—Alternate.
*Internode distance*.—25 mm.

Spurs: (present on 2 yr and older wood):
*Length*.—Varies from 10 to 350 mm.
*Proportion*.—350 mm=1; 200-350 mm=3; 100-200 mm=3; 50-100 mm=3; 10-50 mm=3.
*Width*.—Short; 3.5 mm; Medium: 5 mm; Long: 7 mm.

Flowers at popcorn stage:
*Pedicel*.—Length 12-15 mm; diameter 2 mm.
*Pedicel color*.—Yellow-Green 148D.
*Bud*.—Length 7-9 mm; width 7 mm.
*Bud color*.—Red-Purple 63B, before flower petals expand and open; background of White 155C.

Flowers at full bloom:
*Bloom time*.—Depends on spring temperatures, but with 'Golden Delicious'. 'MAIA1' blooms approximately one week later than parent 'Fuji'.
*Bloom period*.—Depends on spring temperatures but first spur blossoms and then lateral blossoms on one-year wood; approximately 7 days.
*Presentation*.—Showy.
*Fragrance*.—Aromatic.
*Fertility*.—Fertile.
*Corolla diameter*.—35-40 mm.
*Number of flowers per cluster*.—4-6 with 5 typical.

Petals:
*Arrangement*.—Bases overlapping; 5 petals/flower; each petal 15-18 mm length; 12-14 mm width.
*Color*.—Upper surface (inside) White 155C; lower surface (outside) White 155C with Red-Purple 70B overtones pronounced as flower begins to open and then fading as flower completely opens.
*Shape*.—Broadly ovate, abruptly cuneate at junction with receptacle.
*Veins*.—Non-distinct.
*Margins*.—Somewhat ruffled with occasional notching at the apex.
*Texture*.—Soft.
*Receptacle*.—Length 8 mm; width 6 mm; color Green 143D.
*Pedicel*.—Length 18-22 mm; width 2 mm; color Green 143D when pubescent; Reddish tones 58A as pubescence is lost as pedicel matures.
*Sepals*.—5/flower; wedge shaped; sharply pointed; length 6 mm; width 3 mm at widest point (attachment); color Greyed-Green 193B with Reddish Purple tip 58A.
*Stamens*.—18-22 in number.
*Anthers*.—Length 2 mm; width 1.5 mm; color yellow 3D.
*Pollen*.—Present.
*Filaments*.—Length 5-12 mm, increasing in length as flower matures; width 0.5 mm; color Greyed-Green 193B.
*Pistil*.—Held lower than anthers in majority of blossoms.
*Ovary*.—Length 4 mm; width 3 mm; color Green 139B in cross section with Reddish Purple 60A layer under exterior pubescence.
*Style*.—Length 10 mm from fused base to stigmas; width 1.5 mm at fused base; width 0.4 mm as separated styles; pubescent at point of separation from fused base; color Green 143A.
*Stigma*.—Width 1 mm; color Green 143A.

Pollination requirements: Requires cross pollination from diploid varieties with overlapping bloom; will pollinate diploid varieties of overlapping bloom; both pollen and female flowers have been used successfully as parents in MAIA breeding program.

Fruit:
*Maturity when described*.—4 month storage.
*Date of picking*.—Oct. 30, 2011.
*Size*.—Axial diameter 65-70 mm, Transverse diameter 75-80 mm.
*Fruit weight*.—180-220 g, average 200 g.
*Form*.—Roundish oblate regular.
*Cavity*.—Acuminate medium deep; russet extending out of cavity.
*Basin*.—(shape, depth, width) medium depth, medium width, symetrical obtuse regular wavy.
*Calyx*.—Closed reflexed.

Skin:
*Thickness*.—Medium.
*Tendency to crack*.—Little.
*Lenticels*.—Round shape; 0.02-0.08 mm diameter; areolar.
*Color*.—Orange-Red N 34 A.
*Stripes*.—Yes/light striping.
*Ground color*.—Orange-White 159 B.

Flesh:
*Aroma*.—Sweet, aromatic.
*Color*.—Yellow-White 158 C.
*Texture*.—Firm, crisp, breaking, juicy, sweet.
*Eating quality*.—Excellent.

Core: Medium size.

*Bundle area.*—250 mm.

*Bundle.*—Inconspicuous.

*Carpillary area.*—80 mm.

*Seed cells.*—Walls thin, tough.

Seeds:

*Number perfect.*—10.

*Number in one cell.*—2.

*Length.*—9 mm.

*Breadth.*—5 mm.

*Color.*—Greyed-Yellow 162 A; seeds often partially covered with white (presumed calcium) deposits.

Stem:

*Length.*—20-30 mm.

*Width.*—1.8 mm.

*Color.*—Greyed-Yellow 162 A.

Use: Fresh market, dessert.

Shipping quality: Good, subject to stem puncture.

Keeping quality: Excellent.

Tree winter hardiness: Average for an apple variety; depending on acclimation tree is hardy to −10 to −25°.

Drought tolerance: Average for an apple variety. Normal requirements average ½" of rain per week during the growing season.

Disease resistance: Susceptible to apple scab (*Venturia inaequalis*), powdery mildew (*Podosphaera leucotricha*) and other fungal diseases; slight resistance to fireblight (*Erwinia amylovora*); fruit susceptible to soft rot (*Penicillium expansum*).

TABLE 1

Harvest time of 'Honeycrisp' and 'MAIA1', 2008-2011

| Variety | Year 2008 | Year 2009 | Year 2010 | Year 2011 |
|---|---|---|---|---|
| 'Honeycrisp' | 30-Aug. | 1-Sep. | 27-Aug. | 27-Aug. |
| 'MAIA1' | 25-Oct. | 25-Oct. | 22-Oct. | 17-Oct. |

TABLE 2

Fruiting Spur Density on 2-year old wood of 'Fuji' and 'MAIA1', 2011

| Variety | number of spurs/ft of 2-year-old wood |
|---|---|
| 'Fuji' | 1-5 |
| 'MAIA1' | 8-15 |

TABLE 3

Fruit quality data November 2010
FRUIT QUALITY

| Parameter | 'Honeycrisp' | 'Fuji' | 'MAIA1' |
|---|---|---|---|
| weight (g) | 226 | 200.2 | 215 |
| diameter (mm) | 83 | 78.2 | 77.8 |
| length (mm) | 68.5 | 68.5 | 67.9 |
| shape index (l/d) | 0.8253 | 0.876 | 0.8728 |
| cover color | | | |
| % | 75.3 | 81.7 | 90.3 |
| L | 43.2 | 44.9 | 42.8 |
| C | 37.8 | 36.2 | 37.4 |
| h | 33.8 | 32.9 | 30.6 |
| background color | | | |
| % | 24.7 | 18.3 | 9.7 |
| L | 74.9 | 68.7 | 70.9 |
| C | 42.3 | 42.4 | 38.5 |
| h | 101.2 | 93.7 | 99.5 |
| Soluble Solids (%) | 14.3 | 17.2 | 15.6 |
| Titratable Acidity (%) | 4.7 | 4.3 | 5.1 |
| Firmness (kg/cm2) | 7.2 | 7.5 | 7.9 |

What is claimed is:

1. A new and distinct apple tree variety named 'MAIA1', as illustrated and described herein.

* * * * *